United States Patent [19]
Rushton

[11] Patent Number: 6,136,860
[45] Date of Patent: Oct. 24, 2000

[54] USE OF L-LYSINE IN THE TREATMENT OF HAIR LOSS

[75] Inventor: David Hugh Rushton, Rickmansworth, United Kingdom

[73] Assignee: Bio-Scientific Limited, London, United Kingdom

[21] Appl. No.: 09/194,998

[22] PCT Filed: Jun. 6, 1997

[86] PCT No.: PCT/GB97/01542

§ 371 Date: Mar. 15, 1999

§ 102(e) Date: Mar. 15, 1999

[87] PCT Pub. No.: WO97/47276

PCT Pub. Date: Dec. 18, 1997

[30] Foreign Application Priority Data

Jun. 10, 1996 [GB] United Kingdom ............... 9612108

[51] Int. Cl.[7] ............................................. A61K 31/195
[52] U.S. Cl. ...................... 514/561; 514/185; 514/275; 514/474; 514/561; 514/171; 424/647
[58] Field of Search ................................... 514/171, 185, 514/275, 561, 474; 424/647

[56] References Cited

U.S. PATENT DOCUMENTS

| | | |
|---|---|---|
| 3,778,502 | 12/1973 | Aubin et al. . |
| 5,122,369 | 6/1992 | Dye . |
| 5,133,958 | 7/1992 | Stuckler . |
| 5,470,876 | 11/1995 | Proctor . |

FOREIGN PATENT DOCUMENTS

| | | |
|---|---|---|
| 0327263 | 8/1989 | European Pat. Off. . |
| 0 571 198 | 11/1993 | European Pat. Off. . |
| 0652012 | 5/1995 | European Pat. Off. . |
| 0 747 035 | 12/1996 | European Pat. Off. . |
| 2 609 393 | 7/1988 | France . |
| 2 669 224 | 5/1992 | France . |
| 31 18 882 | 1/1983 | Germany . |
| 40 12 148 | 10/1990 | Germany . |
| 720561 | 4/1953 | United Kingdom . |
| 1381649 | 10/1972 | United Kingdom . |
| WO8700427 | 1/1987 | WIPO . |

OTHER PUBLICATIONS

WPIDS AN 1995–171716, Naito, EP 652012, abstract, May 10, 1995.

Embase AN 94173949, Randall, Clinical Endocr 40/4 (43957) abstract, 1994.

Clinical Endocrinology (1994), "Androgens And Human Hair Growth", V. A. Randall, p. 439–457.

Clinical And Experimental Dermatology 1990, "Amino–Acid Composition In Trichorrhexis Nodosa", D. H. Rushton, M. J. Norris & K.C. James, Publication Jul. 24, 1989, p. 24–28.

Derwent AN85–220782, abstract Kanebo, "Hair tonic compsn.—comprising water–soluble salt of dehydroepi–androsterone sulphate", Jul. 29, 1985.

Chemical Abstracts, vol. 83, No. 7, Aug. 18, 1975, Columbus, Ohio, US; abstract No. 57121h, U. Prusiewicz–Witaszek: "Changes in the synthesis of keratin in the hair after supplementing the basic feed of rabbits with methionine and lysine", p. 368.

Primary Examiner—Rebecca Cook
Attorney, Agent, or Firm—Harness, Dickey & Pierce, P.L.C.

[57] ABSTRACT

The use of L-lysine in a composition and method for the prophylaxis and treatment of telogen effluvium is provided. A kit is also provided which includes a plurality of separate containers each containing at least one active agent useful in a combination therapy for said method.

8 Claims, No Drawings

USE OF L-LYSINE IN THE TREATMENT OF HAIR LOSS

This is a 371 of PCT/GB01542 filed Jun. 5, 1997.

The present invention provides a medicament for the prophylaxis and treatment of hair loss, particularly telogen effluvium, in humans. It further provides a kit useful in a combination therapy for the treatment of genetic hair loss.

Scalp hair loss can be divided into the following three main groups and any one group or combinations of said groups may be operating in an individual at any point in time:

1. Hair loss caused by a reduction in the number of hairs per unit area ($cm^2$);
2. Hair loss caused by a reduction in the diameter of hair; and
3. Hair loss caused by an increase in the number of hairs in the telogen (resting) phase, or an increase in the length of time (latency period) between the end of the telogen phase and the initiation of the next anagen (growing) phase.

It is normal to lose some scalp hair each day. There are natural fluctuations in the hair cycle which in turn influence the amount of hair shed from the scalp on a daily basis. It is therefore important to establish if a problem involving excessive hair shedding really exists and that the individual has not just become aware of their normal daily loss.

For most humans, scalp hair has a life cycle of between 1000 and 2000 days (2¾ and 5½ years), following which there is a short period of rest (the telogen phase), which lasts approximately one hundred days. For the majority of its life cycle, scalp hair is in a growth phase known as the anagen phase. As the new hair grows up the follicle it loosens the old resting hair (telogen hair) which is usually dislodged with brushing, combing or shampooing. This cycle continues unless the hair metabolism is disturbed. Since shed hair is almost entirely telogen hair, the loss from the scalp is seen 10 to 12 weeks later.

For normal individuals having 100,000 hairs, the above process results in about 100 hairs per day being lost from the scalp, while for individuals with 150,000 hairs around 150 per day are lost. These figures are for a 1000 day cycle. For a 2000 day cycle, these values would be halved. Scalp hair grows around 0.33 mm per day and with a growth cycle of 1000 days the hair would grow to a length of 33 cm and for 2000 days 66 cm.

Most transient and temporary effects on the hair cycle, which also cause increased hair shedding, correct themselves and no further action is required. Sometimes it is difficult to determine if the natural rate of hair shedding has increased or excessive shedding has declined, since an individual may be unaware of their normal rate. However if a true problem exists, such as occurs in a nutritional imbalance, the consequences can be detected as a reduction in hair volume. This is because the prolonged effect upon the hair cycle causes significant change to the overall amount of hair present.

Many women are aware of an increase in the amount of hair shed daily which will be seen as more hair in the brush, comb, on the bathroom floor, or when they shampoo. When there is no obvious cause (e.g. an illness within the past three months, taking medication known to produce hair loss, or pregnancy), then it is important to consider suboptimal hair growth where increased hair shedding is the primary feature.

The problem of increased hair shedding (telogen effluvium) and suboptimal hair growth principally affects women in the menstrual years and may co-exist with other hair loss disturbances either of a hormonal or nutritional basis. The loss of hair in this condition is the result of an increase in the amount of telogen hair shed from the scalp. It may also involve a reduction in the length of hair grown.

Increased scalp hair shedding results from an excessive amount of telogen hair. Increased hair shedding of this type is usually identified by measuring the ratio of hair in the anagen and telogen phases. In the chronic state there may be no perceived increase in shedding because of a plateau effect in the anagen/telogen ratio, but its consequence is an increase in the number of hairs unable to grow to a given length. Frequently, female sufferers complain of a reduction in the amount of hair they can pin, clip or tie-up, compared to previously. The variable measured to identify this aspect is usually the amount of hair less than 30 mm in length.

Few successful treatments have yet been discovered for the prophylaxis and treatment of hair loss in humans. In particular, no reliable treatment has yet been found for the treatment of telogen effluvium in humans. We have now made the surprising discovery that treatment with the essential amino acid lysine results in a substantial increase in hair growth in patients suffering from hair loss and in particular those suffering from telogen effluvium. Compositions for the treatment of hair loss are disclosed in U.S. Pat. No. 5,470,876, U.S. 5,133,958, U.S. Pat. No. 5,122,369 and DE-A-3118882 which may contain lysine in combination with other ingredients. However, none of these documents discloses the use of L-lysine as an active principle in the prophylaxis or treatment of telogen effluvium.

The present invention provides the use of L-lysine in the manufacture of a medicament for the prophylaxis and treatment of hair loss in humans, provided that said L-lysine is not in the form of a complex with a transition metal and that said medicament does not contain one or more of the following:

(i) a combination of trigonelline and vitamin B6;
(ii) a combination of divalent iron, pantothenic acid and methionine;
(iii) garlic oil or garlic extract.

In particular, L-lysine is especially useful in the manufacture of a medicament for the treatment of telogen effluvium in humans.

Studies involving the administration according to the present invention of L-lysine to women suffering from increased hair shedding show a remarkable increase in scalp hair growth. This hair growth appears to involve an increase in the proportion of growing hair (anagen phase) and an accompanying decrease in the proportion of resting hair (telogen phase), an increase in the length of hair grown (shown as a decrease in the proportion of hair which is less than 30 mm in length) and a reduction in the amount of hair being shed from the scalp.

Typically, the L-lysine is administered in a daily dose of from 200 to 2000 mg, and more usually in a daily dose of 500 to 1500 mg, e.g. in the form of a 500 mg dose administered orally once, twice or three times a day. The L-lysine may be included in a formulation suitable for oral administration which also includes other essential elements, e.g. iron in the form of a salt or chelate such as ferrous sulphate, ferrous fumarate, ferrous gluconate, ferrous succinate, ferrous glycine sulphate or other chelated iron compounds (the typical daily dose of elemental iron being 14 mg to 300 mg); vitamin C (in a quantity equal to the iron content); and vitamin $B_{12}$ (the typical daily dose being 6 $\mu$g to 200 $\mu$g).

L-lysine may conveniently be administered orally, for example as tablets, capsules, granules, powders, mixtures, suspensions or syrups. These formulations can be prepared by conventional means and, if desired, the L-lysine may be mixed with any conventional additive, such an excipient, a binder, a disintegrating agent, a lubricant, a corrigent, a solubilising agent, a suspension aid, an emulsifying agent or a coating agent.

We have also discovered that administration of lysine to patients results in a dramatic increase in the efficacy of known treatments for genetic hair loss (which term covers a number of conditions variously referred to as androgen-dependent alopecia, androgenic alopecia, androgenetic alopecia, common baldness, female baldness, diffuse hair loss and male pattern baldness).

Thus, in a further aspect of the present invention there is provided a kit including a plurality of separate containers, each containing at least one active agent useful in a combination therapy for the treatment of genetic hair loss, wherein said kit includes L-lysine and at least one further active agent selected from minoxidil, anti-androgens, 5α-reductase inhibitors, aromatase inhibitors and corticosteroids.

There is also provided a therapeutic combination for the treatment of genetic hair loss comprising L-lysine and at least one further active agent selected from minoxidil, anti-androgens, 5α-reductase inhibitors, aromatase inhibitors and corticosteroids.

Typical examples of anti-androgens which can be used include cyproterone acetate, spironolactone, medroxyprogesterone acetate and flutamide which can, for example, be formulated for oral or topical administration. Type I, type II or mixed type I and type II 5 α-reductase inhibitors can be used, e.g. finasteride. A typical example of a suitable corticosteroid is dexamethasone.

In a preferred embodiment, the kit comprises L-lysine and at least one further active agent selected from minoxidil and one or more anti-androgens, which are preferably chosen from cyproterone acetate, spironolactone and medroxyprogesterone acetate. In a particularly preferred embodiment, the kit comprises L-lysine which is formulated for oral administration and minoxidil which is formulated for topical application.

The co-administration of L-lysine with known treatments for genetic hair loss such as minoxidil and anti-androgens results in a significant improvement in the efficacy of the treatment. The reason for this improvement in efficacy is not currently understood.

Typically, L-lysine is administered in a daily dose of from 200 mg to 2000 mg, and preferably in a daily dose of 500 to 1500 mg, e.g. in the form of a 500 mg dose administered orally once, twice or three times a day. The known treatment for (genetic hair loss (e.g. topical application of minoxidil to the scalp) is administered concurrently.

The surprising effect of L-lysine in the treatment of various forms of hair loss is illustrated by the following tests.

Treatment of Telogen Effluvium in Women

Eight women were treated over a 16 week period with L-lysine, a 500 mg oral dose being given once, twice or three times a day (500 mg to 1500 mg total daily dose). Various biochemical investigations were performed on the women in the test programme before the start of the said programme and after 16 weeks of therapy, the details of which are given in Table 1 below together with the results obtained (mean values).

The effect of the administration of L-lysine on hair growth was determined by measuring three scalp hair variables—the percentage of hair in the anagen phase, the percentage of hair in the telogen phase and the percentage of hair less than 30 mm in length. These three variables were evaluated using the bio-assay known as the unit area trichogram (see Rushton et al, British Journal of Dermatology, 1990, 123, 187–197; Rushton et al, Clinical and Experimental Dermatology, 1991, 16, 188–192; and Rushton et al, Clinical Endocrinology, 1992, 36, 421–427). The values obtained at the start of the test and after sixteen weeks are shown in Table 2 below.

TABLE 1

| Variable | Time - 0 weeks | Time - 16 weeks | P value |
|---|---|---|---|
| Haemoglobin (hb) | 12.2 | 12.6 | ns |
| Serum ferritin | 50.0 | 49.5 | ns |
| senim zinc | 13.6 | 13.9 | ns |

Blood based variables determined basally and after 16 weeks in eight female subjects complaining of increased hair shedding (mean values obtained, n = 8). Statistical significance was assessed with Student's t-test for paired samples.

TABLE 2

| Variable | Time - 0 weeks | Time - 16 weeks | P value |
|---|---|---|---|
| Anagen % | 82.6 | 88.5 | <0.05 |
| Telogen % | 17.4 | 11.5 | <0.05 |
| Hair <30 mm % | 17.4 | 12.4 | <0.05 |

Hair variables determined basally and after 16 weeks in eight female subjects complaining of increased hair shedding (mean value obtained, n = 8). Statistical significance was assessed with Wilcoxon signed rank test.

The results in Table 2 demonstrate clearly that the administration of L-lysine resulted in an increase in the proportion of hair in the anagen (growth) phase and a corresponding reduction in the proportion of hair in the telogen (resting) phase in women suffering from telogen effluvium. Additionally, there was a significant reduction in the percentage of hair less than 30 mm in length.

The results in Table 1 show that there was no significant change in the haemoglobin, serum ferritin or serum zinc levels in the blood between the start and finish of the treatment. It appears to be reasonable to conclude, therefore, that the significant increase in hair growth observed after the administration of L-lysine to women suffering from telogen effluvium was not due to an increase in the blood iron or zinc level as a result of the administration of L-lysine.

For women suffering from telogen effluvium who have low iron or zinc stores, a further effect was observed, as shown in the following tests.

A group of women exhibiting chronic telogen effluvium who were being treated for reduced iron stores (serum ferritin concentrations below 40ng/ml) failed to achieve adequate increases of serum ferritin despite taking an iron supplement containing 50 to 100 mg of iron per day. However, when a daily L-lysine supplement of 1.0 g or 1.5 g was added to their existing daily iron supplement a significant (P<0.002) increase in serum ferritin concentration was observed (Table 3).

TABLE 3

Serum ferritin concentration basal and after 4 or 6 months of treatment with 50 mg twice daily with and without L-lysine (1 to 1.5 g) daily.

| | | | Serum Ferritin levels | |
| --- | --- | --- | --- | --- |
| | | | After 4 or 6 months of treatment | |
| | Age | Baseline (ng/ml) | Iron only 100 mg/day (ng/ml) | Iron (100 mg/day) + (Lysine 1 or 1.5 g/day) |
| Subject 1 | 69 | 10.90 | 12.20 | 27.60 |
| Subject 2 | 32 | 31.00 | 41.00 | 80.00 |
| Subject 3 | 34 | 13.00 | 15.00 | 50.00 |
| Subject 4 | 51 | 35.00 | 26.00 | 71.00 |
| Subject 5 | 44 | 27.00 | 38.00 | 59.00 |
| Subject 6 | 31 | 7.00 | 15.00 | 37.00 |
| | Mean | 20.7 | 24.5 | 54.1 |
| | | | P = 0.3 [iron only (NS)] | P < 0.002 (iron + lysine) |

(statistical analysis paired Student's t test)

In Table 4 below serum zinc concentrations are presented for a group of women (n=10) in whom basal concentrations were below 11.8 $\mu$mol/L, i.e. within 10% of the lower limit of normal. The mean baseline concentration for this group was 10.28 $\mu$mol/L (range 9.0 $\mu$mol/L to 11.7 $\mu$mol/L). Each was treated with a daily supplement of L-lysine (1 g to 1.5 g) for 16 weeks, following which the mean serum zinc concentration had increased significantly (P<0.001) to 13.78 $\mu$mol/L (range 11.6 to 17.4 $\mu$mol/L).

TABLE 4

Changes in serum zinc concentration following daily supplementation with 1 g–1.5 g of L-lysine over a 16 week period.

| Patient | Serum Zinc Time 0 | Serum Zinc After 16 weeks |
| --- | --- | --- |
| Subject 1 | 11.7 | 17.4 |
| Subject 2 | 10.4 | 16.1 |
| Subject 3 | 10.6 | 11.6 |
| Subject 4 | 9.3 | 11.8 |
| Subject 5 | 11.7 | 13.3 |
| Subject 6 | 9.0 | 13.8 |
| Subject 7 | 9.5 | 14.5 |
| Subject 8 | 9.0 | 14.0 |
| Subject 9 | 10.3 | 12.3 |
| Subject 10 | 11.3 | 13.0 |
| Mean | 10.28 | 13.78 |

P < 0.001 paired t test

Treatment of Women Suffering from Genetic Hair Loss

The effect of the administration of lysine on the efficacy of known treatments for genetic hair loss was investigated as follows.

Women suffering from genetic hair loss, all of whom had adequate iron stores within the normal range at the start of the test (i.e. serum ferritin levels of greater than 40 mg/ml) were divided into four groups.

The first group (17 women) was treated with minoxidil only (in the form of a topical formulation comprising 3% minoxidil by weight).

The second group (15 women) had a combined treatment of minoxidil (again as a topical formulation comprising 3% minoxidil by weight) and an oral anti-androgen chosen from cyproterone acetate, medroxyprogesterone and spironolactone. The first two anti-androgens were administered in combination with ethinylestradiol or an oral contraceptive. The particular anti-androgen administered was chosen on the basis of clinical need.

The third group (8 women) received a combined treatment of minoxidil (again as a topical formulation comprising 3% minoxidil by weight) and 500 to 1500 mg per day of L-lysine (administered orally).

The fourth group (13 women) received a combined treatment comprising minoxidil (again as a topical formulation comprising 3% minoxidil by weight), an oral anti-androgen (administered as to the second group above) and 500 to 1500 mg per day of L-lysine (administered orally). The results of these tests are shown in Table 5 below.

TABLE 5

| Response | | |
| --- | --- | --- |
| | Minoxidil Only | Minoxidil + Anti-androgens Only |
| + | 9/17 (52.9%) | 11/15 (73.%) |
| = | 6/17 (35.3%) | 3/15 (20.0%) |
| − | 2/17 (11.8%) | 1/15 (67%) |
| | L-lysine + Minoxidil | L-lysine + Minoxidil + Anti-androgens |
| + | 8/8 (100%) | 13/13 (100%) |
| = | None | None |
| − | None | None |

Response key
+ patient noticed an increase in hair quantity.
= patient did not see any change in hair quantity.
− patient felt there had been a decrease in hair quantity.

The results in Table 5 suggest that the co-administration of L-lysine to patients being treated for genetic hair loss with known treatments such as the topical administration of minoxidil and/or the oral administration of anti-androgens results in a considerable improvement in the efficacy of these known treatments.

When L-lysine is administered for the treatment of telogen effluvium in humans according to the present invention, a typical daily treatment regimen could include:

L-lysine at 200 mg to 2000 mg per day;
Elemental iron at 14 mg to 300 mg;
Vitamin C at 14 mg to 300 mg; and
Vitamin $B_{12}$ at 3 $\mu$g to 24 $\mu$g.

Typically, the L-lysine may be administered as tablets or capsules containing the following ingredients:

200 mg L-lysine
14 mg Vitamin C
14 mg iron (as ferrous glycine sulphate)
3 $\mu$g Vitamin $B_{12}$ Typically, 200 mg L-lysine tablets are administered six times daily during the acute phase of telogen effluvium, four times daily during chronic phase and two times daily as a maintenance dose.

What is claimed is:

1. A method for the treatment or prophylaxis of telogen effluvium in a human, consisting of administering to said human in need of said method an effective amount of L-lysine.

2. A method for the treatment or prophylaxis of telogen effluvium in a human, comprising administering to a human in need of said method a composition comprising of an effective amount of L-lysine and one or more of the following:

(i) an iron compound selected from the group consisting of iron (II) sulphate or a chelated iron compound, the daily dosage of elemental iron being 14 mg to 300 mg;
(ii) vitamin C in a daily dosage of 14 mg to 300 mg;
(iii) vitamin $B_{12}$ in a daily dosage of 3 $\mu$g to 24 $\mu$g.

3. The method according to claim 1, wherein said effective amount of L-lysine consists of a daily dosage of 200 mg to 2000 mg.

4. The method according to claim 1, wherein said chelated iron compound is selected from the group consisting of iron (II) fumarate, iron (II) gluconate, iron (II) succinate and iron (II) glycine sulphate.

5. A pharmaceutical composition for the prophylaxis or treatment of telogen effluvium in a human, said composition containing from 200 mg to 2000 mg of L-lysine and one or more of the following:
   (i) an iron compound selected from the group consisting of iron (II) sulphate or a chelated iron compound, the amount by weight of elemental iron being 14 mg to 300 mg;
   (ii) from 14 mg to 300 mg of vitamin C; and
   (iii) from 3 µg to 24 µg of vitamin $B_{12}$.

6. The pharmaceutical composition according to claim 5, wherein said chelated iron compound is selected from the group consisting of iron (II) fumarate, iron (II) gluconate, iron (II) succinate and iron (II) glycine sulphate.

7. A kit comprising a plurality of at least four separate containers differing from each other, wherein at least one of said containers contains from 200 mg to 2000 mg of L-lysine, at least one different container contains an iron compound selected from the group consisting of iron (II) sulphate or a chelated iron compound, the amount of elemental iron being 14 mg to 300 mg, at least one still different container contains from 14 mg to 300 mg of vitamin C, and at least one yet different container contains from 3 µg to 24 µg of vitamin $B_{12}$.

8. The kit according to claim 7, wherein said chelated iron compound is selected from the group consisting of iron (II) fumarate, iron (II) gluconate, iron (II) succinate and iron (II) glycine sulphate.

* * * * *